(12) United States Patent
Brinz et al.

(10) Patent No.: US 7,378,852 B2
(45) Date of Patent: May 27, 2008

(54) MEASURING DEVICE HAVING A PLURALITY OF POTENTIOMETRIC ELECTRODE PAIRS SITUATED ON A SUBSTRATE

(75) Inventors: Thomas Brinz, Bissingen A.D. Teck (DE); Jane Lewis, Castle Square (GB)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 11/015,887

(22) Filed: Dec. 17, 2004

(65) Prior Publication Data

US 2005/0151541 A1 Jul. 14, 2005

(30) Foreign Application Priority Data

Dec. 17, 2003 (DE) ............... 103 59 173

(51) Int. Cl.
*G01N 27/416* (2006.01)
*G01N 27/26* (2006.01)

(52) U.S. Cl. .................. 324/438; 204/433

(58) Field of Classification Search ............... 324/438, 324/425; 435/4, 6, 287, 287.1, 287.2, 288.5; 205/777.5, 780.5, 787.5, 782; 204/547, 643, 204/433, 430, 400; 422/58, 82.05
See application file for complete search history.

(56) References Cited

U.S. PATENT DOCUMENTS

| | | | | |
|---|---|---|---|---|
| 4,124,475 A | * | 11/1978 | Zetter et al. ................. 204/412 |
| 4,447,775 A | * | 5/1984 | Breuker et al. .............. 324/438 |
| 4,595,486 A | * | 6/1986 | Schmidt et al. .............. 204/412 |
| 4,948,490 A | * | 8/1990 | Venkatasetty ............... 204/412 |
| 5,034,192 A | * | 7/1991 | Wrighton et al. ......... 422/82.02 |
| 5,045,163 A | * | 9/1991 | Nyberg et al. ............ 205/792.5 |
| 5,376,255 A | * | 12/1994 | Gumbrecht et al. ........ 204/426 |
| 5,483,164 A | * | 1/1996 | Moss et al. .................. 324/425 |
| 5,837,446 A | * | 11/1998 | Cozzette et al. ................ 435/6 |
| 5,958,791 A | * | 9/1999 | Roberts et al. ............. 436/514 |
| 6,391,471 B1 | * | 5/2002 | Hiraoka et al. ............. 428/623 |
| 6,506,594 B1 | * | 1/2003 | Barany et al. ........... 435/287.2 |
| 6,579,434 B1 | * | 6/2003 | Cornell et al. .............. 204/416 |
| 6,663,756 B2 | * | 12/2003 | Lee et al. .................... 204/415 |
| 6,682,638 B1 | * | 1/2004 | Prohaska et al. ........... 204/426 |
| 6,740,518 B1 | * | 5/2004 | Duong et al. ............ 435/287.2 |
| 6,746,583 B2 | * | 6/2004 | Lee et al. ................. 204/403.1 |
| 6,756,148 B2 | * | 6/2004 | Hojo et al. .................... 429/35 |
| 2003/0012693 A1 | * | 1/2003 | Otillar et al. .................. 422/58 |
| 2003/0087453 A1 | * | 5/2003 | Scheying et al. ........... 436/151 |
| 2003/0175947 A1 | * | 9/2003 | Liu et al. ................. 435/288.5 |

(Continued)

FOREIGN PATENT DOCUMENTS

| | | |
|---|---|---|
| DE | 44 24 213 | 1/1996 |
| DE | 195 15 065 | 2/1996 |
| DE | 298 00 998 | 4/1998 |

*Primary Examiner*—Andrew H Hirshfeld
*Assistant Examiner*—Hoai-An D Nguyen
(74) *Attorney, Agent, or Firm*—Kenyon & Kenyon LLP

(57) ABSTRACT

A measuring device having a plurality of potentiometric electrode pairs situated on a substrate is described. One of the electrodes of each electrode pair represents a reference electrode and the other electrode represents a pH-sensitive working electrode. The electrode pairs form an interdigital structure, and the substrate is covered by a mask in such a way that the individual electrode pairs are separated from one another at least in the area of the interdigital structures of the electrode pairs.

11 Claims, 3 Drawing Sheets

U.S. PATENT DOCUMENTS

| | | | |
|---|---|---|---|
| 2004/0011650 A1* | 1/2004 | Zenhausern et al. | 204/547 |
| 2004/0023253 A1* | 2/2004 | Kunwar et al. | 435/6 |
| 2004/0063152 A1* | 4/2004 | Gumbrecht et al. | 435/7.1 |
| 2004/0238360 A1* | 12/2004 | Scheying et al. | 204/433 |
| 2004/0248282 A1* | 12/2004 | Sobha et al. | 435/287.2 |
| 2004/0262151 A1* | 12/2004 | Scheying et al. | 204/230.2 |
| 2005/0031926 A1* | 2/2005 | Sugimasa et al. | 429/30 |
| 2005/0089993 A1* | 4/2005 | Boccazzi et al. | 435/286.2 |

* cited by examiner

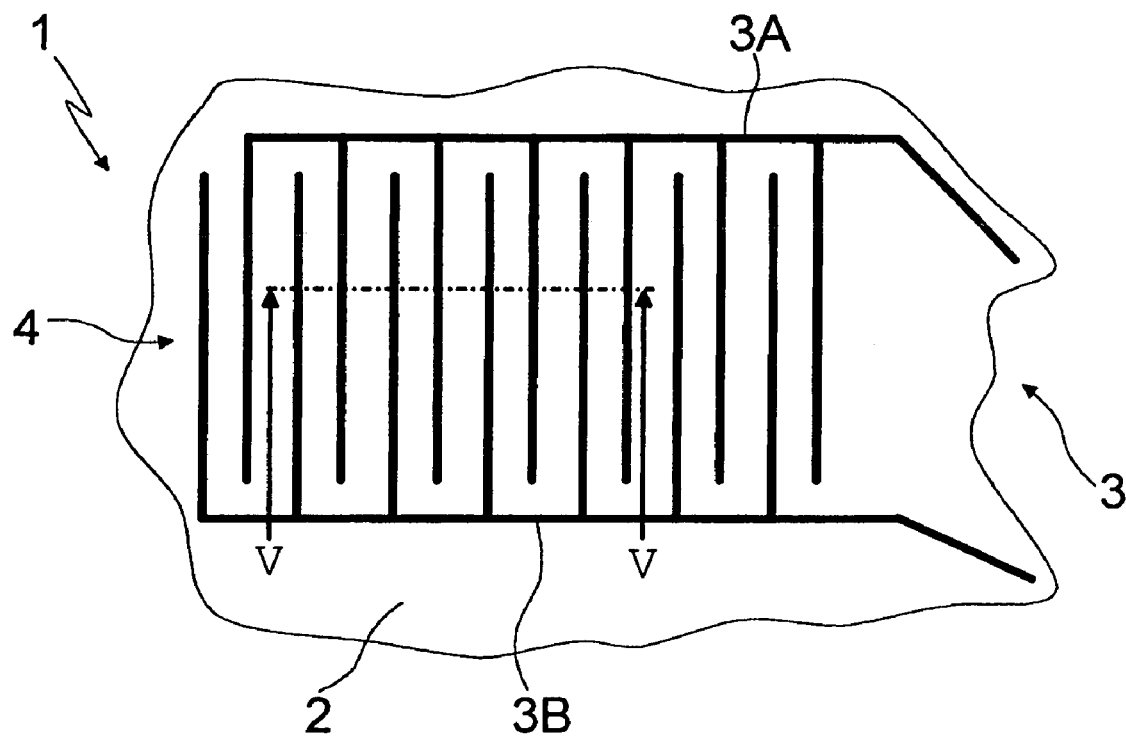
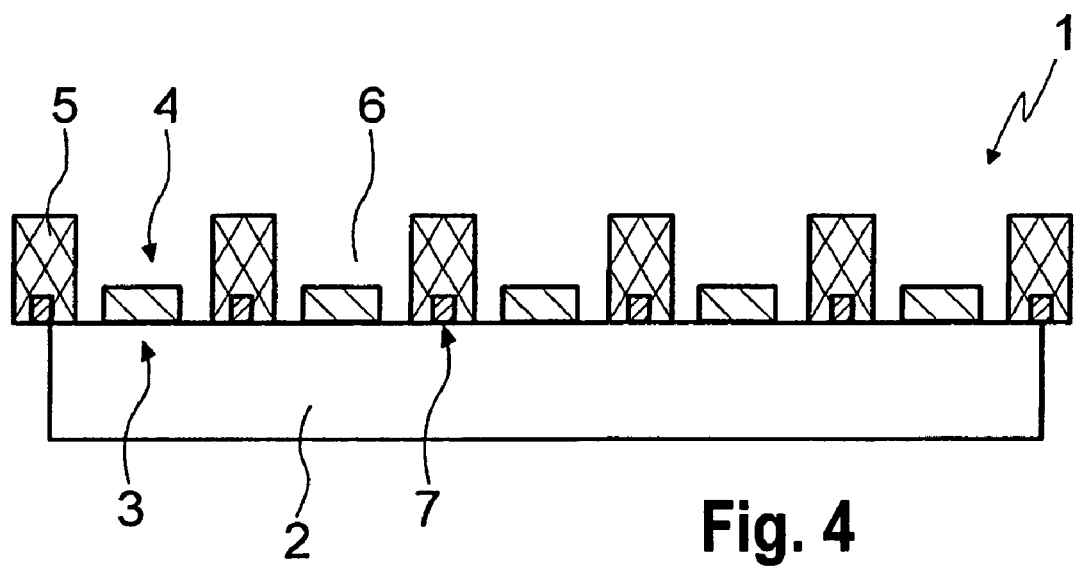

MEASURING DEVICE HAVING A PLURALITY OF POTENTIOMETRIC ELECTRODE PAIRS SITUATED ON A SUBSTRATE

FIELD OF THE INVENTION

The present invention relates to a measuring device having a plurality of potentiometric electrode pairs situated on a substrate, one of the electrodes of each electrode pair representing a reference electrode and the other electrode representing a pH-sensitive working electrode.

BACKGROUND INFORMATION

Measuring devices known from industry such as electrochemical sensors or the like are used, for example, for determining a pH value of a liquid medium or even for determining a carbon dioxide component of a medium. Measuring devices designed for such purposes include potentiometric electrode pairs which may be constructed in different ways.

German Patent Application No. 44 24 213, German Published Patent Application No. 195 15 065, and German Published Patent Application No. 298 00 998 describe potentiometric sensors whose operation is based on the long-known principle that an electric voltage, which changes with the change in a chemical species concentration, is measurable between at least two electrodes. The electric voltage to be measured is induced by an electric potential difference resulting from a difference in the chemical equilibrium potential of the individual electrodes with their environment. This voltage is determined using the sensors known from the above-mentioned related art, which are designed using a pH-sensitive glass electrode as the working electrode and a reference electrode.

In chemical and pharmaceutical research, when investigating processes and also certain materials, high throughput development is performed, in which a plurality of syntheses may be performed in a known manner in parallel reactors under different process conditions in a cost-effective manner within a short period of time, and may be evaluated automatically. The use of a larger number of parallel reactors is, however, at the same time associated with a high degree of measurement complexity and with a number of the above-mentioned electrode pairs which is at least equal to the number of parallel reactors, in order to be able to monitor all parallel reactors simultaneously. At least one electrode pair is associated with each of the parallel reactors for reaction checking and reaction tracking.

Due to the large number of measuring points in the high throughput development, the equipment costs for process checking and process tracking are disadvantageously high, and the large space required by the electrode pairs in the area of the parallel reactors results in the parallel reactors having large dimensions. In order to reduce the equipment costs, there is always the possibility of limiting the number of glass electrodes and measuring the individual parallel reactors sequentially, for example.

This procedure, however, does not provide continuous tracking of the processes in the parallel reactors, which reduces the time advantage of the high throughput development. In addition, the glass electrodes must be cleaned when changing from one parallel reactor to the next one, which makes handling of such a system disadvantageously difficult.

SUMMARY OF THE INVENTION

Using the measuring device according to the present invention having a plurality of potentiometric electrode pairs situated on a substrate, parallel reaction checking and reaction tracking of a plurality of syntheses running in parallel may be advantageously performed in a cost-effective manner. Furthermore, the design of the measuring device allows for simple handling and reduced dimensions.

This is achieved by forming an interdigital structure on each of the electrode pairs situated on the substrate, these structures being separated by a mask situated on the substrate. In this way, not only are the potentiometric electrode pairs required for process tracking and evaluation situated on the substrate, but also the parallel reactors required for the syntheses running in parallel and having compact dimensions are also provided there. A plurality of syntheses may thus be carried out, monitored, and supplied to an analyzer device simultaneously in the least possible space and in a simple manner.

BRIEF DESCRIPTION OF THE DRAWINGS

FIG. 3 shows an enlarged detail of an area III of FIG. 2.

FIG. 4 shows a highly schematic sectional view of the measuring device according to FIG. 1 along line IV-IV.

DETAILED DESCRIPTION

Figure 1:
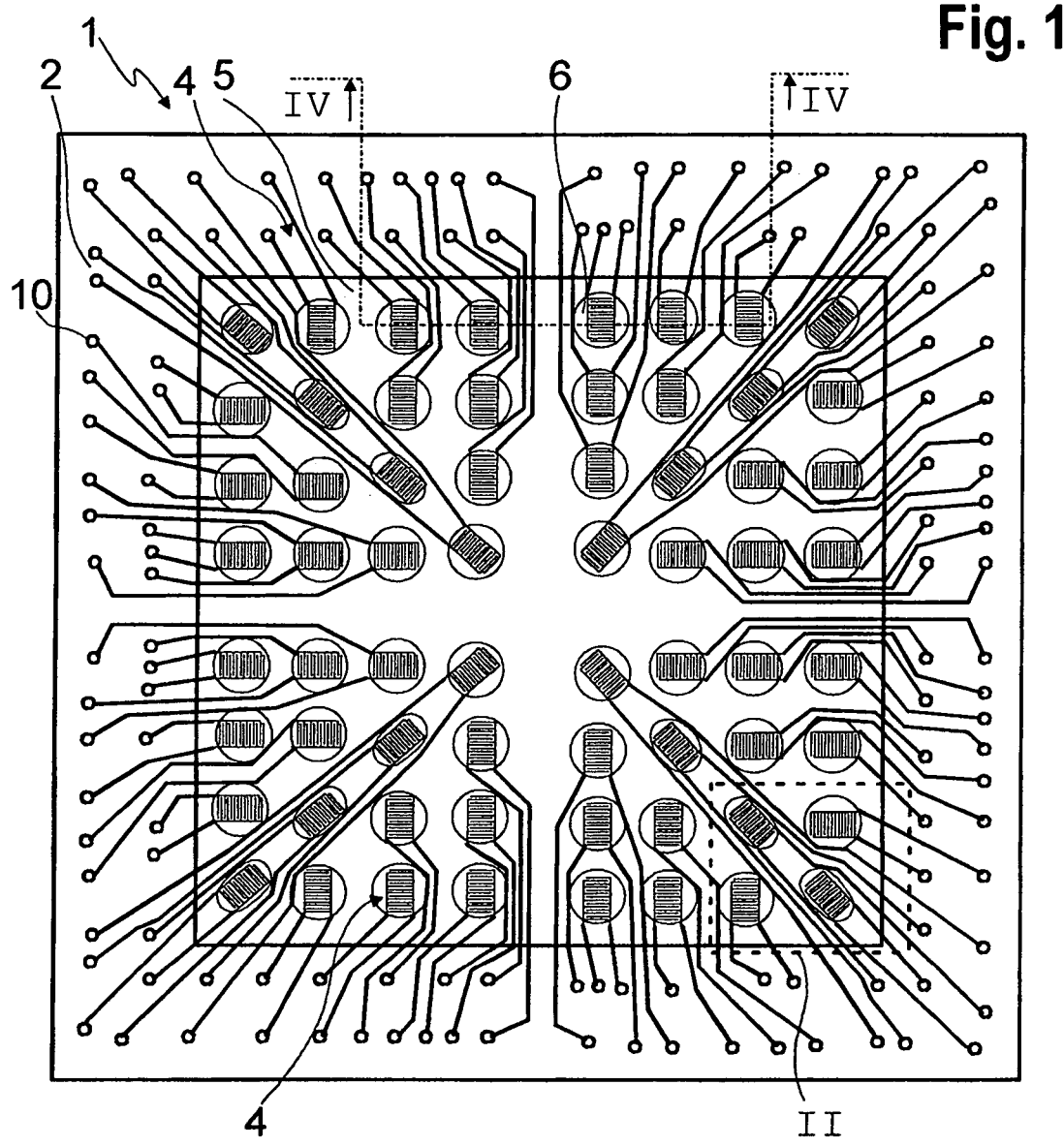
FIG. 1 shows a top view of a measuring device designed according to the present invention.

FIG. 1 shows a top view of a measuring device 1, using which preferably simultaneous pH measurements may be performed during high throughput development where a plurality of different individual syntheses run simultaneously in parallel reactors. Using measuring device 1 having a plurality of potentiometric sensor devices preferably working by the Severinghaus principle, a plurality of reactions running simultaneously or sequentially may thus be continuously tracked in a cost-effective manner in minimum space.

Measuring device 1 has a substrate 2, on which 64 potentiometric sensor devices are situated, each having a potentiometric electrode pair 3. Substrate 2 is designed here as a ceramic foil made of low-temperature sintering glass-ceramic substrate such as a low-temperature cofiring ceramic (LTCC), which is characterized by a very low electrical conductivity and very good mechanical stability. Alternatively, the substrate may also be manufactured of aluminum oxide, aluminum nitride, silicon dioxide, or a wafer of silicon, silicon nitride, or the like.

Figure 2:
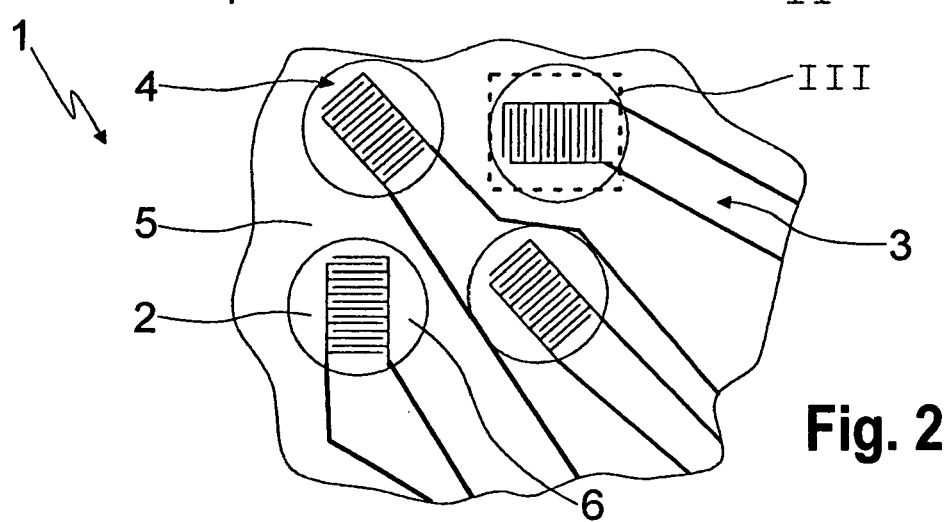
FIG. 2 shows an enlarged detail of an area II of FIG. 1.

Electrode pairs 3 having an interdigital comb structure, i.e., an interdigital structure 4, shown in more detail in FIGS. 2 and 3, are applied to substrate 2 using thick-layer technology, electrode pairs 3 being applied here via a screen printing process in the form of pastes made of electrode material. The above-mentioned electrode pastes are formed from the particular electrode material in powder form and an inorganic or organic vehicle, the electrode material powder being dispersed in the vehicle during the manufacture of the pastes.

Electrodes having a layer height between preferably 10 Φm and 20 Φm, depending on the properties of the screen, are applied to the substrate during the screen printing process. Subsequently the pasty electrodes are fired together with substrate 2 in a firing process, a permanent bond being formed between substrate 2 and electrode pairs 3 and the paste vehicle being evaporated.

Alternatively, the electrodes of electrode pairs 3 may also be applied to substrate 2 using another printing process known from thick layer technology, such as template printing, foil printing, or inkjet printing.

One of electrodes 3A schematically depicted in FIGS. 1 through 3 is designed as a reference electrode, and the other electrode 3B is designed as a pH-sensitive working electrode, reference electrode 3A being made of silver and working electrode 3B being made of iridium dioxide.

Of course, one skilled in the art may also choose to manufacture working electrode 3B of electrode pairs 3 from antimony oxide. In selecting the electrode materials, it must be ensured that the electrode material used is characterized by a certain electrical conductivity, so that an excessive voltage drop does not occur over the measuring path, i.e., the internal resistance of the entire measuring cell is less than that of the measuring medium, and that it may be applied to substrate 2 in a cost-effective manner using one of the above-mentioned methods.

The structure of the potentiometric sensor device, i.e., measuring device 1 made up of electrode pairs 3 and substrate 2, obtained after the firing process, may also be used for the subsequent manufacturing process during which a mask 5 is applied to the substrate.

Alternatively, there is also the possibility of treating the side of measuring device 1 provided with electrode pairs 3, before applying mask 5, using an electrochemical oxidation process in an HCl or HBr bath or another halide ion bath to oxidize the surface of the silver electrodes, i.e., reference electrodes 3A of electrode pairs 3 to a silver halide, thereby passivating it. Undesirable reactions of the pure silver electrode with the medium to be monitored, whose pH value is to be measured, are thus prevented or considerably reduced. If the passivating layer of silver electrode 3A is a silver chloride layer, the halogenated area of silver electrode 3A has a low material exchange equilibrium with the environment, which results in a particularly stable electrode.

The iridium oxide electrodes, i.e., working electrodes 3B of electrode pairs 3, are not modified during the halogenating process of reference electrodes 3A, and remain in their unmodified form. Potentiometric electrode pairs 3 designed this way, which are used for pH measurements, are characterized by an almost ideal Nernst response (Delta_E=−0.059 V*pH), making it possible to perform very accurate measurements even without signal conversion.

After manufacture of the ready-to-use electrode pairs 3 on substrate 2, mask 5 is now applied to substrate 2 and electrode pairs 3. In this case, mask 5 is made of a synthetic material and may alternatively also be made of stainless steel or glass. Furthermore, mask 5 has openings 6 in the area of interdigital structures 4 of electrode pairs 3, so that interdigital structures 4 of electrode pairs 3 are not covered by mask 5, and it is possible to bring the medium to be monitored by an electrode pair 3 in contact with interdigital structure 4 of this electrode pair 3.

Openings 6 in mask 5 are designed in such a way that mask 5 forms reaction vessels, i.e., cavities, in the area of interdigital structures 4 of electrode pairs 3, which are open on the side of mask 5 facing away from substrate 2 and have substrate 2 and on top of this an interdigital structure 4 of an electrode pair 3 as the reactor bottom.

Figure 6:
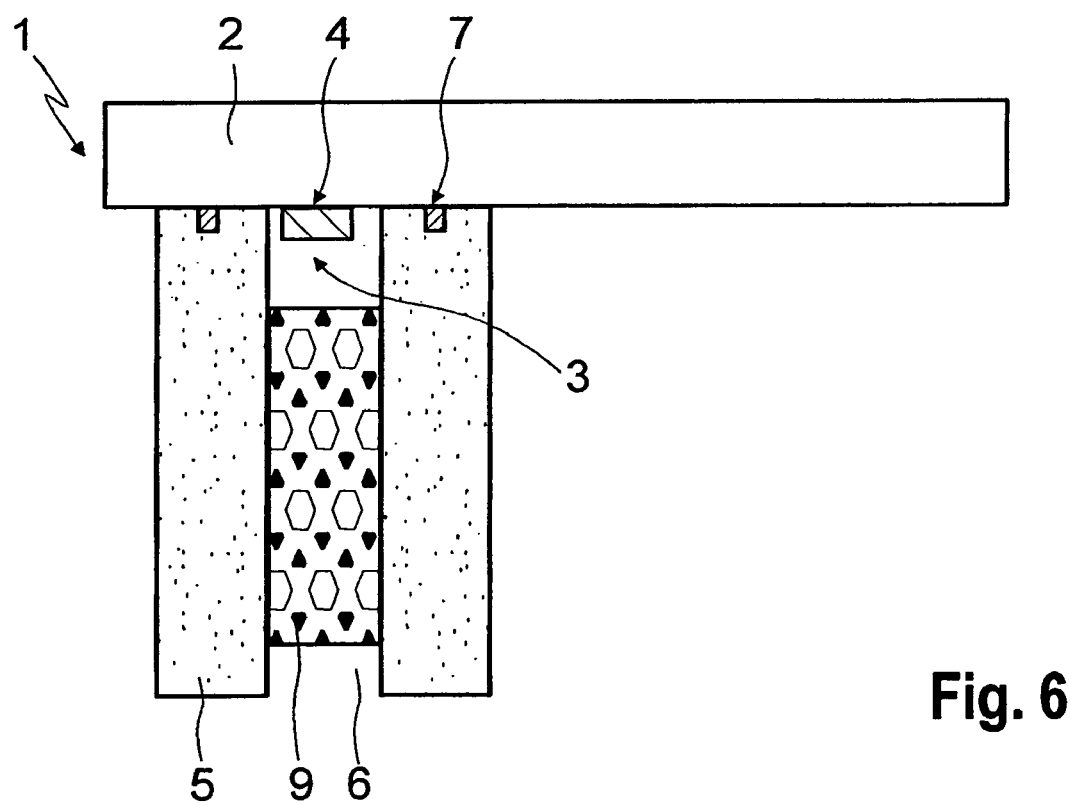
FIG. 6 shows a highly schematic partial view of an embodiment of the measuring device according to the present invention allowing a pH value of gaseous media to be determined.

Mask 5 is sealed against electrode pairs 3 and substrate 2 on its side facing electrode pairs 3 and substrate 2 by gaskets 7, which are integrated into mask 5 as shown in FIGS. 4 and 6. Gaskets 7 are manufactured here from a chemically inert material, preferably from a fluorinated rubber or tetrafluoroethylene.

In addition to interdigital structures 4, contact points 10 (shown in detail in FIG. 1) of electrode pairs 3 are also not covered by mask 5, so that the potential difference between reference electrode 3A and working electrode 3B of each electrode pair 3 of measuring device 1 may be supplied to an analyzer circuit, which is associated with measuring device 1 and not shown in detail in the drawing, via essentially known spring contacts or spring clamps. In this manufacturing step of measuring device 1, measuring device 1 is basically completed and usable for monitoring a plurality of (here 64) different systems. For this purpose, each of openings 6 in mask 5 forming a reaction vessel above interdigital structures 4 of electrode pairs 3 is filled with a liquid medium. The pH values of the media introduced are then determined simultaneously or sequentially.

Using measuring device 1 according to the present invention, there is the possibility, for example, of simultaneously investigating different motor oils which have been exposed preferably to different aging processes prior to the measurement, the measuring device according to the present invention being of course also suitable for determining the pH of other media.

Thus, using an advantageous embodiment of measuring device 1 according to the present invention, syntheses whose media chemically react upon direct contact with the previously described electrode materials of the reference electrode and working electrode may also be monitored. Because such reactions may disadvantageously result in distortion of the measurement result, electrode pairs 3 are provided with a cover layer 8 illustrated in FIG. 5 at least in the area of openings 6 in mask 5. Interdigital structures 4 of electrode pairs 3 are chemically isolated by cover layer 8 from a medium to be tested.

Figure 5:
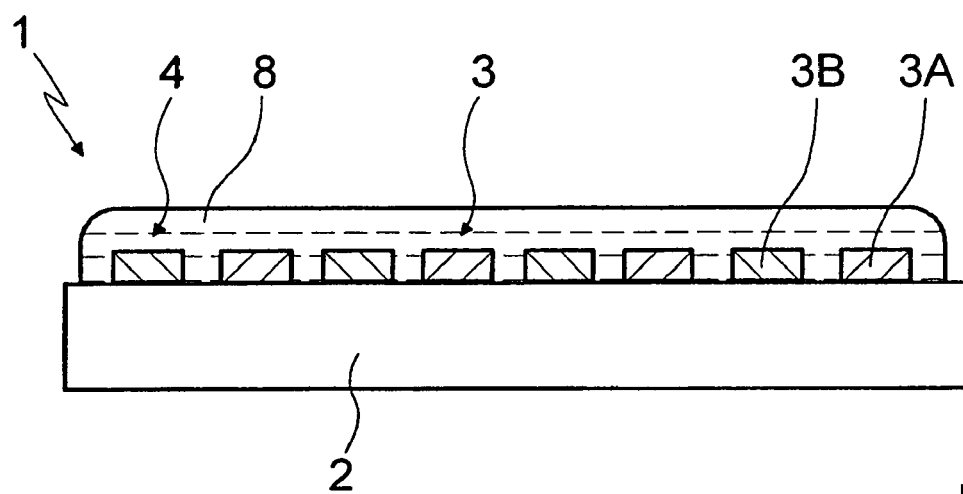
FIG. 5 shows a highly schematic partial sectional view of the interdigital structure of electrodes according to FIG. 3 along line V-V, the electrode pairs being additionally provided with a cover layer.

The illustration of measuring device 1 in FIG. 5 represents a partial sectional view of interdigital structure 4 of an electrode pair 3 along line V-V of FIG. 3. Interdigital structure 4 is completely covered by cover layer 8 as shown, whereby direct contact between reference electrode 3A and working electrode 3B with the liquid medium to be monitored located in opening 6 of mask 5 above it, and a chemical reaction between the medium and electrode pair 3 provided with cover layer 8 are prevented.

At the same time, the pH value of the medium located above cover layer 8 is established in cover layer 8, allowing the pH value to be determined. This is achieved if cover layer 8 is made of a suitable polymer electrolyte, for example. If cover layer 8 is also to protect interdigital structure 4 of an electrode pair 3 underneath it against abrasive attack, cover layer 8 may also be designed as a porous glass diaphragm layer.

Measuring device 1 according to the present invention is, however, also usable for pH measurement in gaseous media. For this purpose, in a refinement of the object of the present invention, a polymer diaphragm 9 is situated over interdigital structures 4 of electrode pairs 3 in openings 6 of mask 5 as shown in FIG. 6, this diaphragm, which responds sensitively to carbon dioxide, covering interdigital structure 4.

Using a measuring device 1 designed in this way, catalytic reactions for example with carbon dioxide may be tracked, it being possible to detect in general any gas that is acidic or basic or forms acidic or basic products through reactions with a suitable acceptor using a measuring device 1 designed according to FIG. 6.

What is claimed is:

1. A measuring device, comprising:
    a substrate;
    a mask;
    a plurality of potentiometric electrode pairs situated on the substrate, one of the electrodes of each electrode pair representing a reference electrode and the other electrode representing a pH-sensitive working electrode;
    chemically inert gaskets provided between the mask and the electrodes and between the mask and the substrate, wherein:
    the electrode pairs in each case form an interdigital structure, and the substrate is covered by the mask in such a way that the individual electrode pairs are separated from one another at least in an area of the interdigital structure of the electrode pairs.

2. The measuring device as recited in claim 1, wherein the mask is designed such that a cavity delimited by the mask is formed over each interdigital structure.

3. The measuring device as recited in claim 1, wherein a surface of the mask, a surface of the substrate and a surface of at least one of the electrodes form an opening.

4. The measuring device as recited in claim 1, wherein the gaskets are made of one of fluorinated rubber and tetrafluoroethylene.

5. The measuring device as recited in claim 1, wherein:
    the mask is made of one of a synthetic material, stainless steel, and glass, and
    the mask has openings in an area of the interdigital structure and electrical contact points electrodes of the electrode pairs exposing the interdigital structures and the contact points.

6. The measuring device as recited in claim 5, wherein the interdigital structures are provided with a cover layer in an area of the openings, the cover layer chemically isolating the interdigital structure from a medium to be tested and permitting a pH value to be determined.

7. The measuring device as recited in claim 6, wherein the cover layer includes one of a polymer electrolyte and a porous glass diaphragm.

8. The measuring device as recited in claim 1, wherein the substrate is a ceramic substrate, and wherein the electrodes of the electrode pairs are made of materials which can be applied to the ceramic substrate using screen printing.

9. The measuring device as recited in claim 8, wherein the working electrode includes one of an $IrO_2$ electrode and an SbO electrode.

10. The measuring device as recited in claim 8, wherein the reference electrode includes one of an AgCl/Ag electrode and an AgBr/Ag electrode.

11. The measuring device according to claim 1, wherein the mask is configured with at least one opening such that the mask forms at least one reaction vessel and wherein the electrode pair and the substrate are configured to form a reactor bottom and wherein the electrode pair is in direct contact with a medium to be monitored by the electrode pair in the reaction vessel.

* * * * *